United States Patent
Fukuzono et al.

(10) Patent No.: US 6,326,189 B1
(45) Date of Patent: *Dec. 4, 2001

(54) NUCLEIC ACID SEPARATING VESSEL, A METHOD OF MANUFACTURING THE NUCLEIC ACID SEPARATING VESSEL, AND A METHOD FOR SEPARATING THE NUCLEIC ACID

(75) Inventors: Shinichi Fukuzono, Hitachinaka; Tetsuo Yokoyama, Tokyo; Yukiko Ikeda, Chiyoda-machi; Yoshishige Endo, Tsuchiura, all of (JP)

(73) Assignee: Hitachi, Ltd., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/518,172

(22) Filed: Mar. 2, 2000

(30) Foreign Application Priority Data

Mar. 4, 1999 (JP) .................................. 11-056846

(51) Int. Cl.$^7$ ..................................................... C12M 1/34
(52) U.S. Cl. .................................. 435/287.2; 435/288.1; 435/288.6; 210/198.2; 210/502.1; 210/510.1; 210/263; 210/321.75; 210/321.84; 95/88; 96/107
(58) Field of Search ..................................... 210/635, 656, 210/658, 198.2, 502.1, 510.1, 321.75, 321.84, 473, 416.1, 91, 134, 263; 95/82, 88; 96/101; 422/101; 435/2, 6, 91.1, 91.2, 91.32, 91.4, 91.51, 287.2, 288.1, 288.6

(56) References Cited

U.S. PATENT DOCUMENTS

| | | | |
|---|---|---|---|
| 1,669,362 | * | 5/1928 | Watson . |
| 5,145,806 | * | 9/1992 | Shirakawa et al. ..................... 501/80 |
| 5,360,544 | * | 11/1994 | Nakaso et al. ........................ 210/483 |
| 5,645,723 | * | 7/1997 | Fujishiro et al. ............... 210/321.75 |
| 6,162,356 | * | 12/2000 | Ikeda et al. ....................... 210/198.2 |

FOREIGN PATENT DOCUMENTS

| | | | |
|---|---|---|---|
| 35-9230605-A | * | 12/1984 | (JP) . |
| 36-3295444-A | * | 12/1988 | (JP) . |
| 40-2022120-A | * | 1/1990 | (JP) . |
| 40-2137715-A | * | 5/1990 | (JP) . |

OTHER PUBLICATIONS

Proc. Natl. Acad. Sci. USA, vol. 76, No. 2, Feb. 1979, "Preparative and analytical purification of DNA from agarose", B. Vogelstein et al, pp. 615–619.

\* cited by examiner

*Primary Examiner*—David A. Redding
(74) *Attorney, Agent, or Firm*—Mattingly, Stanger & Malur, P.C.

(57) ABSTRACT

The sample vessel 1 comprises plurality of vessels 1*a*. The vessel 1*a* comprises an opening for sample inlet 3, a liquid sample outlet 4, and a silicon oxide composite particles structural body 2 is arranged at the bottom of the vessel 1*a*, i.e. the liquid sample outlet 4.

The silicon oxide composite particles structural body 2 is a structural body composed of a composite made of plural silicon oxide particles having smaller diameter combined with a resin particle having larger diameter. Accordingly, even if the diameter of the silicon oxide particles 7 is set small in order to maintain the nucleic acid combination ability high, the presence of the resin particles 6 having a large diameter makes it possible to ensure the liquid conduction path, and the nucleic acid separating vessel, which is capable of suppressing decrease of the B/F separating velocity with maintaining the nucleic acid combining ability high can be realized.

3 Claims, 6 Drawing Sheets

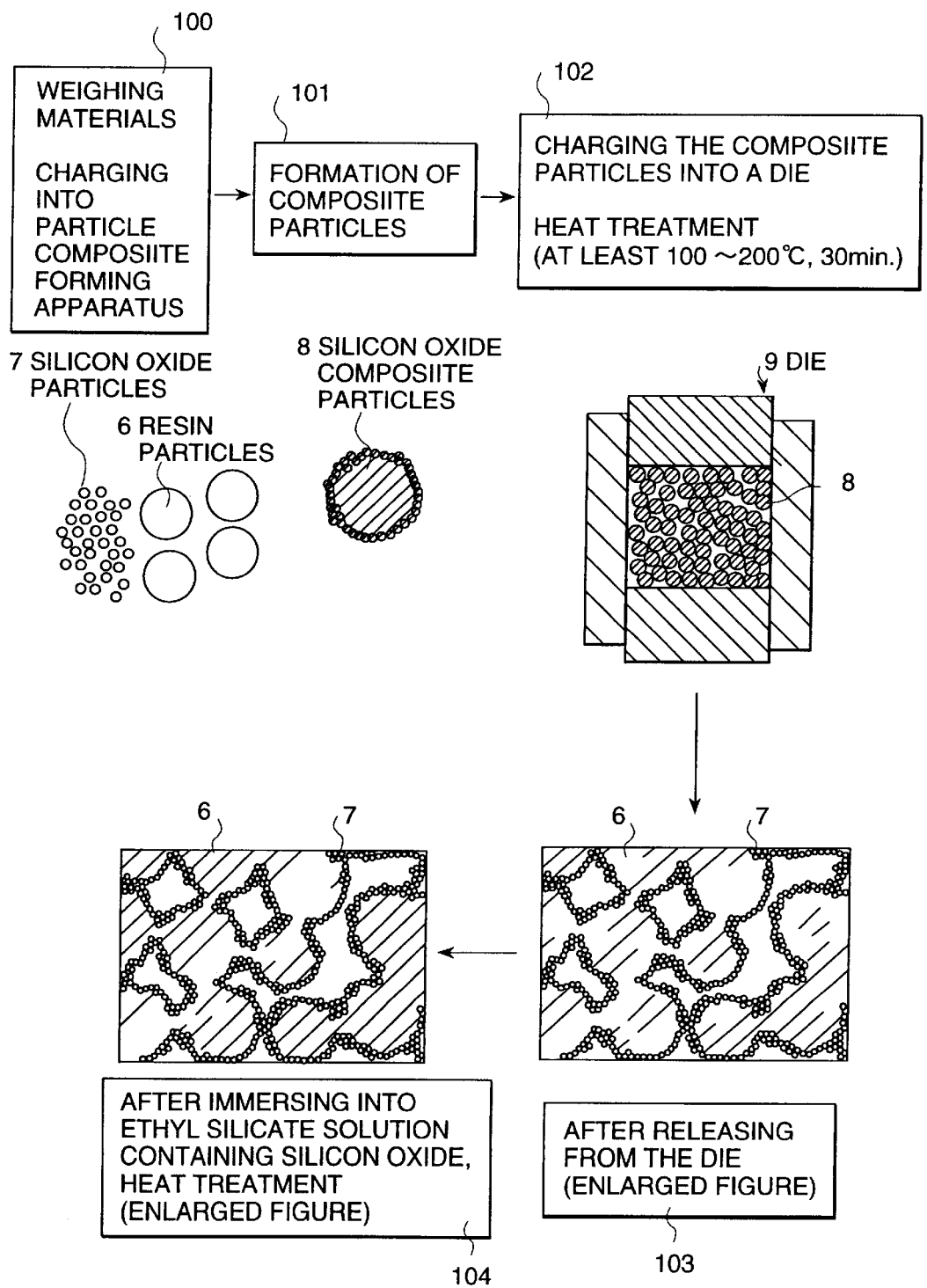

NUCLEIC ACID SEPARATING VESSEL, A METHOD OF MANUFACTURING THE NUCLEIC ACID SEPARATING VESSEL, AND A METHOD FOR SEPARATING THE NUCLEIC ACID

BACKGROUND OF THE INVENTION

The present invention relates to a nucleic acid separating vessel for separating the nucleic acid from a liquid sample, to a method of manufacturing the same, and to a method for separating the nucleic acid.

A conventional method for separating and purifying a nucleic acid comprising the steps of isolating the nucleic acid into a liquid sample by making a biological sample and the like soluble in the solution, extracting the nucleic acid with an organic solvent and the like, precipitating the nucleic acid with alcohol and the like, and recovering the nucleic acid, has been used widely.

However, the above conventional method is inadequate for automatic operation, in view of requiring a large amount of labor and learning the operating procedures, and of frequent use of centrifugal separating operation, because it requires a large number of operating steps.

In order to overcome the above problems, a method utilizing an adsorption characteristics of the nucleic acid to a solid phase body has been disclosed. For instance, a description that the nucleic acid combines with glass under the presence of chaotropic salt is disclosed in the Proceedings of National Academy of Science of the USA vol. 76, 615–619 (1979).

Utilizing the characteristics of the nucleic acid to combine with a silicon oxide (silica) under a certain condition, a nucleic acid extracting kit and a nucleic acid automatic extracting apparatus using magnetic silica particles, silica particles, silica fiber or filter, spin column or micro plate containing the above articles, and the like are obtainable commercially.

However, in accordance with the above prior art, a magnet is necessary for separating the magnetic particles from the liquid sample (B/F separation) when the magnetic particles are used, and a centrifugal separating operation is necessary when the glass particles or spin column is used. Accordingly, the operation and composition of the apparatus become composite. In particular, when the magnetic particles were used in a micro plate type, magnetic particle separating mechanisms as same number as the number of wells became necessary, and there were problems such that the composition of the apparatus becomes composite and expensive.

In a case when silica fiber or filter, and micro plate containing them are used, the B/F separation is performed by a filtering operation or a centrifugal operation. When particle size was decreased, or fiber density was increased in order to increase combining ability of these materials with nucleic acid, there were problems such that passing velocity of the liquid sample was decreased, and the velocity of the B/F separation was decreased.

SUMMARY OF THE INVENTION

One of the objects of the present invention is to realize a nucleic acid separating vessel, which is capable of suppressing decrease of the B/F separating velocity with maintaining the nucleic acid combining ability high.

Other one of the objects of the present invention is to realize a method of manufacturing the nucleic acid separating vessel, which is capable of suppressing decrease of the B/F separating velocity with maintaining the nucleic acid combining ability high.

Other one of the objects of the present invention is to realize a method for separating nucleic acid using the nucleic acid separating vessel, which is capable of suppressing decrease of the B/F separating velocity with maintaining the nucleic acid combining ability high.

In order to realize these objects, the present invention is composed as follows:

(1) A nucleic acid separating vessel for separating the nucleic acid from a biological sample provided with a silicon oxide composite particle structural body as a separating means for separating the nucleic acid from a biological sample; wherein a silicon oxide composite particle is formed by making silicon oxide group particles form a composite with surface of a particle, which is larger than the silicon oxide group particle and becomes a nucleus; and the plural silicon oxide composite particles are combined each other three dimensionally to form the silicon oxide composite particle structural body.

(2) Preferably, the plural nucleic acid separating vessels described in the above (1) are arranged on a same supporting plate to form a nucleic acid separating vessel assembly.

(3) A method for separating nucleic acid from a biological sample comprising the steps of: charging samples containing nucleic acid into the nucleic acid separating vessel described in the above (1) or the nucleic acid separating vessel assembly described in the above (2); combining the nucleic acid in the sample with the silicon oxide composite particle structural body of the nucleic acid separating vessel; washing the silicon oxide composite particle structural body, whereon the nucleic acid is combined; and releasing and recovering the nucleic acid from the silicon oxide composite particle structural body.

(4) Preferably, the particle which becomes a nucleus described in the above (1) is a resin particle.

(5) As described previously, the diameters of the silicon oxide particles and the resin particle can be set arbitrary. However, in view of forming the composite structure, the diameter of the silicon oxide group particle is preferably smaller than $\frac{1}{10}$ of the resin particle which becomes a nucleus described in the above (1). In accordance with the size of the micro plate, the maximum diameter of the resin particle is restricted to substantially 9 mm, and in view of problems in handling the particles such as scattering at mixing the particles, the minimum diameter of the silicon oxide particle is preferably at least 1 nm, that is, $\frac{1}{9,000,000}$ of the diameter of the resin particle.

(6) A method for manufacturing the nucleic acid separating vessel for separating nucleic acid from a biological sample comprising the steps of: forming a silicon oxide composite particle by making silicon oxide group particles form a composite with surface of a particle, which is larger than the silicon oxide group particle and becomes a nucleus; packing the plural silicon oxide composite particles into a die of a designated shape; forming the silicon oxide composite particle structural body having the designated shape by heating the die to melt and combine the plural silicon oxide composite particles each other three dimensionally; and assembling the silicon oxide composite particle structural body having the designated shape with a main body of the nucleic acid separating vessel as a nucleic acid separating portion.

BRIEF DESCRIPTION OF THE DRAWINGS

FIG. 1 is a set of drawings indicating an embodiment of the present invention; FIG. 2 indicates an example of separable nucleic acid separating vessels, FIG. 4 is schematic illustrations for explaining the manufacturing method of the silicon oxide composite particles structural body.

DESCRIPTION OF THE PREFERRED EMBODIMENTS

Hereinafter, a nucleic acid separating vessel is explained as the first embodiment of the present invention.

Figure 1A:
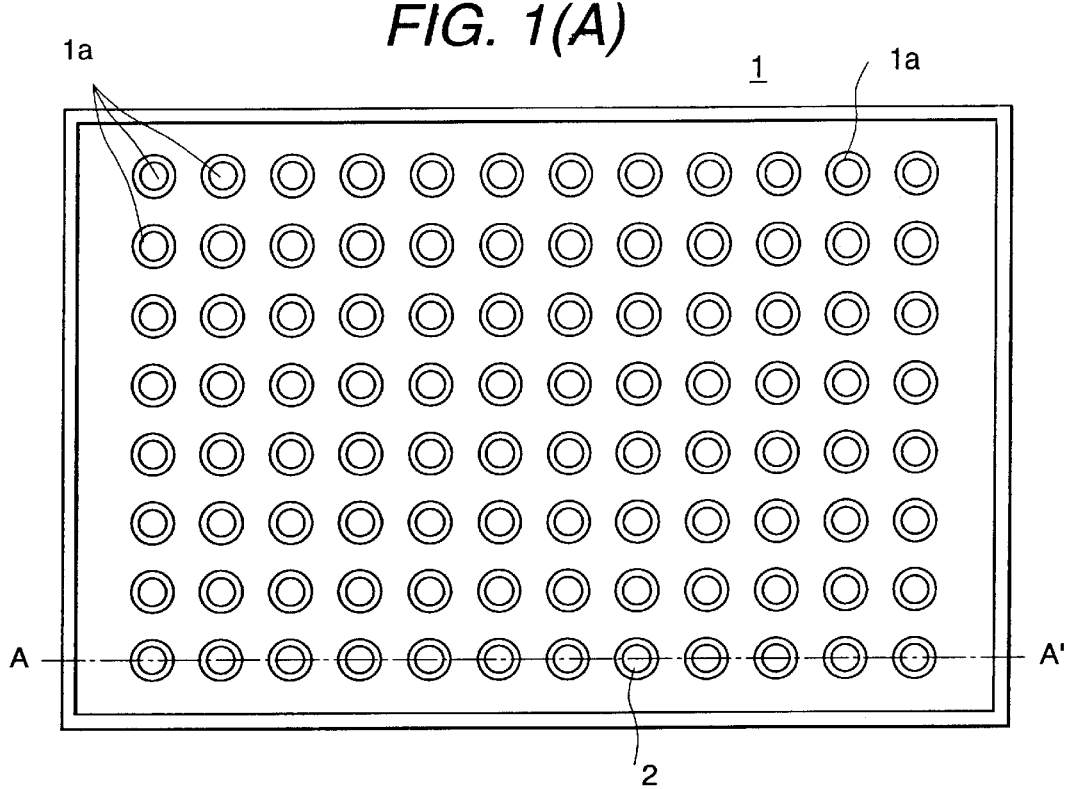
FIG. 1(A) is a schematic plan view of sample vessels, wherein plural vessels having a same shape called as micro plate are arranged on a same supporting plate.
Figure 1B:
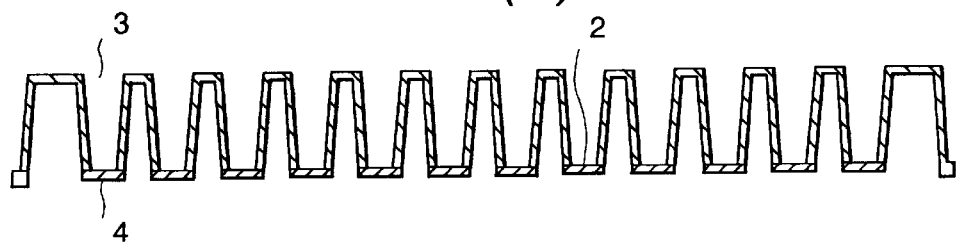
FIG. 1(B) is a cross section of the same.

FIG. 1(A) is a plan view of a sample vessel (nucleic acid vessel assembly), wherein plural vessels 1a having a same shape called as micro plate are arranged on a supporting plate, and FIG. 1(B) is a cross section taken along the line A–A' in FIG. 1(A).

The sample vessel 1 in FIG. 1(A) comprises the plural vessels 1a, and the vessel 1a comprises an opening for sample inlet 3 and a liquid sample outlet 4. The silicon oxide composite particles structural body 2, which is explained in details later, is arranged at the bottom (nucleic acid separating means)of the vessel 1a, which is the liquid sample outlet 4.

The manufacturing method of the silicon oxide composite particles structural body 2 is explained hereinafter.

FIG. 4 is a set of schematic illustrations for explaining the manufacturing method of the silicon oxide composite particles structural body 2. In the step 100 in FIG. 4, resin particles 6 (particle diameter 180–1000 μm) and silicon oxide particles 7 (average particle diameter 4–5 μm) are weighed so that the weight of the silicon oxide particles becomes 0.2–10% by weight to the weight of the resin particles 6. The weighed particles 6 and 7 are charged into a well known particle composite forming apparatus for forming a composite.

In the step 101, the silicon oxide composite particles 8 are formed by the particle composite forming apparatus. The silicon oxide composite particle 8 is a composite particle, which is composed by burying plural silicon oxide particles 7 having a smaller diameter than the resin particle into the resin particle 6 having a larger diameter as indicated in FIG. 4.

In the step 102, a designated amount of the silicon oxide composite particles 8 is charged into a die 9 made of PTFE (polytetrafluoroethylene). The charged die 9 is heated at a temperature in the range of 100° C.–200° C. (higher than a heat resistance temperature of the resin particles 6) for approximately 30 minutes in order to combine the resin particles 6 each other three dimensionally by fusion. The die 9 is a die for forming the silicon oxide composite particle structural body 2 in the shape indicated in FIG. 1.

In the step 103, the structural body is taken out from the die 9. An enlarged cross section of the structural body taken out from the die 9 is shown in FIG. 4. Then, in the step 104, the structural body taken out from the die 9 is immersed into an ethyl silicate solution (a sol-gel solution containing silicon compound: an alcoholic solution of silicon alkoxide; ethyl silicate 25 g, water 17.28 g, hydrochloric acid (12 N) 0.3 g, adjusted with ethyl alcohol 5.42 g), wherein silicon oxide particles 7 having smaller diameter (particle diameter: 40–300 nm) is mono-dispersed, at room temperature for one minute. Then, the structural body is taken out from the solution. An enlarged cross section of the structural body taken out from the solution is shown in FIG. 4.

Subsequently, an excess solution of the structural body taken out from the solution is wiped off lightly, or blow off by a blower, and dried by air or at 40° C.–50° C. Then, a heat treatment of the structural body is performed at 100° C.

Depending on necessity, the same steps to immerse into the ethyl silicate solution and to dry by air as the above steps are repeated several times.

The structural body 2 formed by the steps explained above is assembled with a sample vessel main body, wherein the portions other than the structural body 2 are manufactured previously, at the portion corresponding to the bottom of the vessel 1a (nucleic acid separating portion) by press fitting or adhesion, and the like.

In accordance with the manufacturing method indicated in FIG. 4, the silicon oxide composite particles 8 are formed by forming a composite mechanically with the silicon oxide particles 7 and the resin particles 6. However, the composite particles can be formed with the silicon oxide particles 7 and the resin particles 6 by other method.

Because the resin particle 6 is softer than the silicon oxide particle 7, a condition that the silicon oxide particles 7 are buried into the surface of the resin particles 6 is generated by forming the composite. That means, a film like structure composed of the silicon oxide particles 7 is formed on the surface of the resin particles 6. Accordingly, the properties of the resin particles themselves are varied. As one of the changed properties, an apparent heat resistance temperature is improved. Therefore, the temperature for the heat treatment in the step 102 is preferably selected slightly higher than the heat resistance temperature of the untreated resin particles 6.

In accordance with the manufacturing method described previously, the surface of the flow path of the structural body 2 is treated after forming the structural body 2 by immersing into an ethyl silicate solution containing the silicon oxide particles 7 having a small diameter. In this case, the silicon oxide particles 7 having a small diameter are combined with the silicon oxide particle portions, which are generated by forming the composite, by the ethyl silicate as a binder. Accordingly, the silicon oxide particles 7 are combined with the resin particles 6 tightly, and the structural body 2, the silicon oxide particles of which is not split off from the resin particles 6, can be obtained.

In accordance with repeating the procedure of immersing the structural body 2 into the ethyl silicate solution and drying by air and the like for several times as described previously, the surface of the resin particles can be decorated with the silicon oxide particles 7, and an effect of non-specific combination of the nucleic acid with the resin particles 6 can be decreased. However, the decoration is restricted as much as not to fill spaces formed by the resin particles themselves for ensuring liquid conduction.

In accordance with the nucleic acid separating method of the present invention, a biological sample (test piece) containing the nucleic acid is charged into the sample vessel 1. In this case, because the sample vessel comprises plural vessels 1a, plural test pieces can be charged simultaneously into the plural vessels 1a. In accordance with passing the biological sample solution mixed with a combining solution containing chaotropic ions through the structural body 2 of the vessel 1a, the nucleic acid in the sample is combined with the structural body 2. The structural body 2 combined with the nucleic acid is washed with a washing liquid, which does not release the nucleic acid combined with silicone oxide, for instance a washing liquid containing ethy alcohol. Subsequently, the nucleic acid is recovered by releasing from the structural body 2 using water or a releasing liquid having an adequate buffer function.

In accordance with the sample vessel 1 manufactured as explained above, liquid conduction is ensured and decrease in passing velocity of the liquid sample can be suppressed. Because, even if the diameter of the silicon oxide particles 7 is set small in order to maintain the nucleic acid combination ability high, the presence of the resin particles having a large diameter makes it possible to combine the silicon oxide composite particle structural bodies 2 each other, which is the composite of the silicon oxide particles 7 and the resin particles 6, by fusion.

Therefore, the nucleic acid separating vessel, which is capable of suppressing the decrease of the B/F separating velocity with maintaining the high nucleic acid combination ability, can be realized.

And, a manufacturing method of the nucleic acid separating vessel, which is capable of suppressing the decrease of the B/F separating velocity with maintaining the high nucleic acid combination ability, can be realized.

In accordance with the manufacturing method of the nucleic acid separating vessel by the present invention, the vessel can be formed in an arbitrary shape because the resin particles are used as the particles having a large diameter, and an advantage that the present invention can be applied to various shaped vessels is realized.

Furthermore, a nucleic acid separating method using the nucleic acid separating vessel, which is capable of suppressing the decrease of the B/F separating velocity with maintaining the high nucleic acid combination ability, can be realized.

Figure 2:
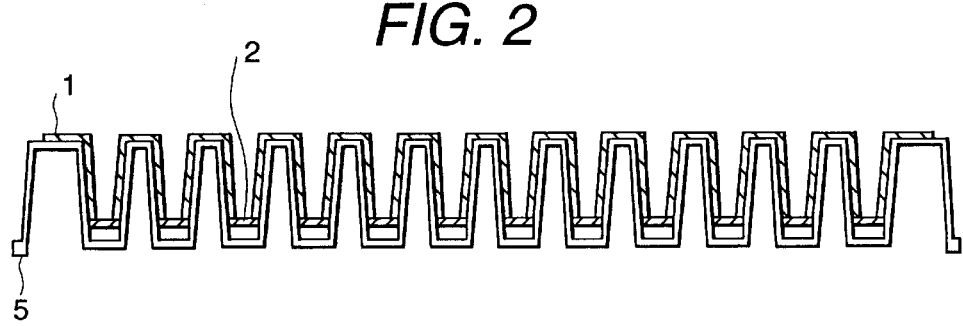
FIG. 2 is a schematic cross section of the nucleic acid separating vessels, which indicates the second embodiment of the present invention.

FIG. 2 is a cross section of a nucleic acid separating vessels relating to the second embodiment of the present invention. In accordance with the second embodiment, the bottom portion of the sample vessel 1 is composed of the silicon oxide composite particle structural body 2 as same as the first embodiment, but a micro plate is used as the recovering vessel 5.

Because the upper portion of the sample vessel 1 in the second embodiment is as same as the portions indicated in FIG. 1, the portion is not shown in FIG. 2.

As the method for fixing the silicon oxide composite particle structural body 2 to the sample vessel 1, a press fitting method, an adhesion method using a non-permeable adhesive agent, a method by deformation the sample vessel 1 with heat or pressure, and the like, as same as the first embodiment. In addition to the above examples, a method by encapsulating the silicon oxide composite particle structural body 2 into the sample vessel 1 using mesh, filter, and the like, which does not disturb the liquid conduction, can be used.

In any cases, the presence of the silicon oxide composite particle structural body 2 at one plane in the cross section of the sample vessel 1 is preferable, so as to make the liquid sample containing the nucleic acid pass effectively through the silicon oxide composite particle structural body 2. In order to increase the capturing ratio of the nucleic acid, plural silicon oxide composite particle structural bodies 2 can be fixed in a sample vessel 1.

In accordance with the embodiment shown in FIG. 2, the same advantages as the embodiment shown in FIG. 1 can be realized.

FIGS. 3(A)–(D) indicate four examples of the shapes of the nucleic acid separating vessels for separating the nucleic acid from samples.

Figure 3A:
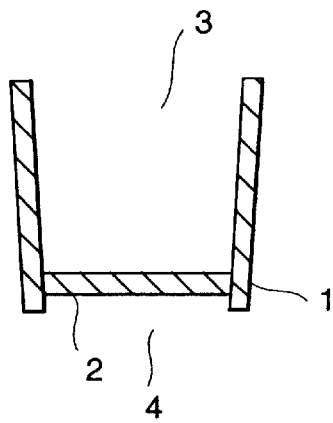
FIG. 3 is a set of drawings indicating examples of shapes of the nucleic acid separating vessels, which are capable of separating and purifying nucleic acid from a sample.

FIG. 3(A) indicates a cross section of a nucleic acid separating vessel 1a for separating the nucleic acid from a sample, wherein the bottom of the vessel 1a is formed with the silicon oxide composite particle structural bodies 2.

Figure 3B:
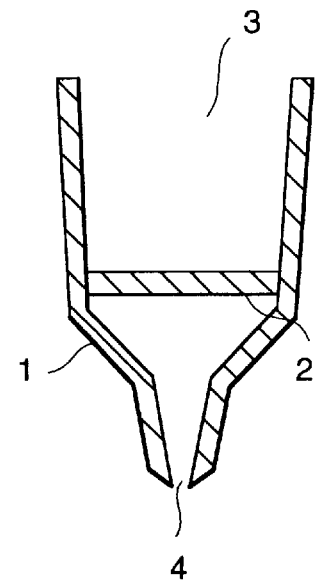

FIG. 3(B) indicates a cross section of a nucleic acid separating vessel 1a, wherein the silicon oxide composite particle structural bodies 2 formed in a plate shape is fixed at an intermediate portion of the opening of the sample inlet 3 and the liquid sample outlet 4. The shape of the nucleic acid separating vessel 1a is formed so that the diameter of the flow path is decreased in accordance with closing the liquid sample outlet 4 from the opening 3, and the diameter of the liquid sample outlet 4 is smaller than the diameter of the opening 3. The liquid sample passing through the structural body 2 can be released to a small region by forming the shape of the liquid sample outlet 4 as described above, and the shape is convenient for recovering the liquid sample.

Figure 3C:
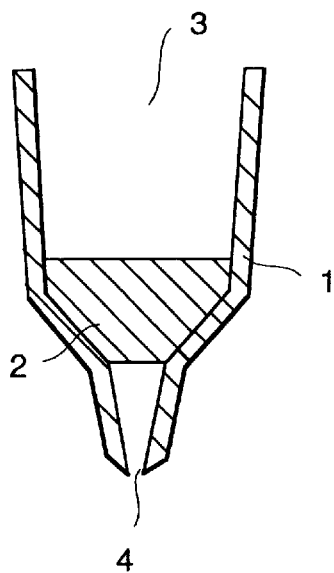

FIG. 3(C) indicates a cross section of a nucleic acid separating vessel 1a, wherein the outer shape of the separating vessel 1a is as same as the vessel shown in FIG. 3(B), but the silicon oxide composite particle structural bodies 2 formed so as to coincide with the inner shape of the sample vessel 1 is fixed at an intermediate portion of the opening of the sample inlet 3 and the liquid sample outlet 4.

In the case shown in FIG. 3(C), the passing velocity of the liquid sample becomes slower than the case shown in FIG. 3(B), but it is effective when the increased recovering amount of the nucleic acid is required.

Figure 3D:
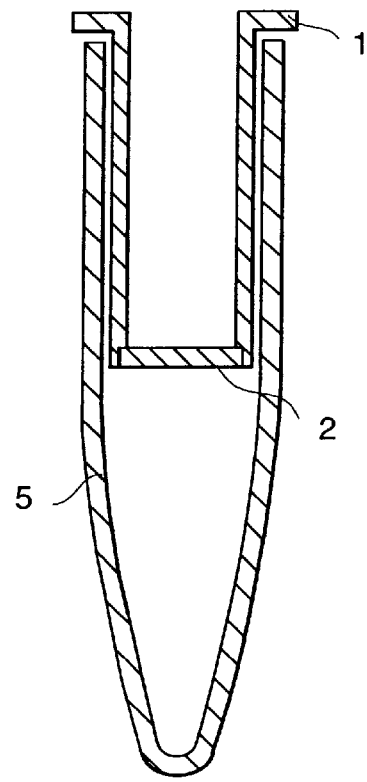

FIG. 3(D) indicates a cross section of a nucleic acid separating vessel 1a, wherein the sample vessel 1 is formed in a shape which made it possible to insert the sample vessel 1 in the recovering vessel 5, and the silicon oxide composite particle structural body 2 is fixed in the inert type sample vessel 1a.

The above examples indicated in FIGS. 3(A)–(D) can be plural vessels 1a composing the sample vessel 1 indicated in FIG. 1, or, not a composing portion of the sample vessel 1, but can be a single independent vessel for separating the nucleic acid.

Figure 5:
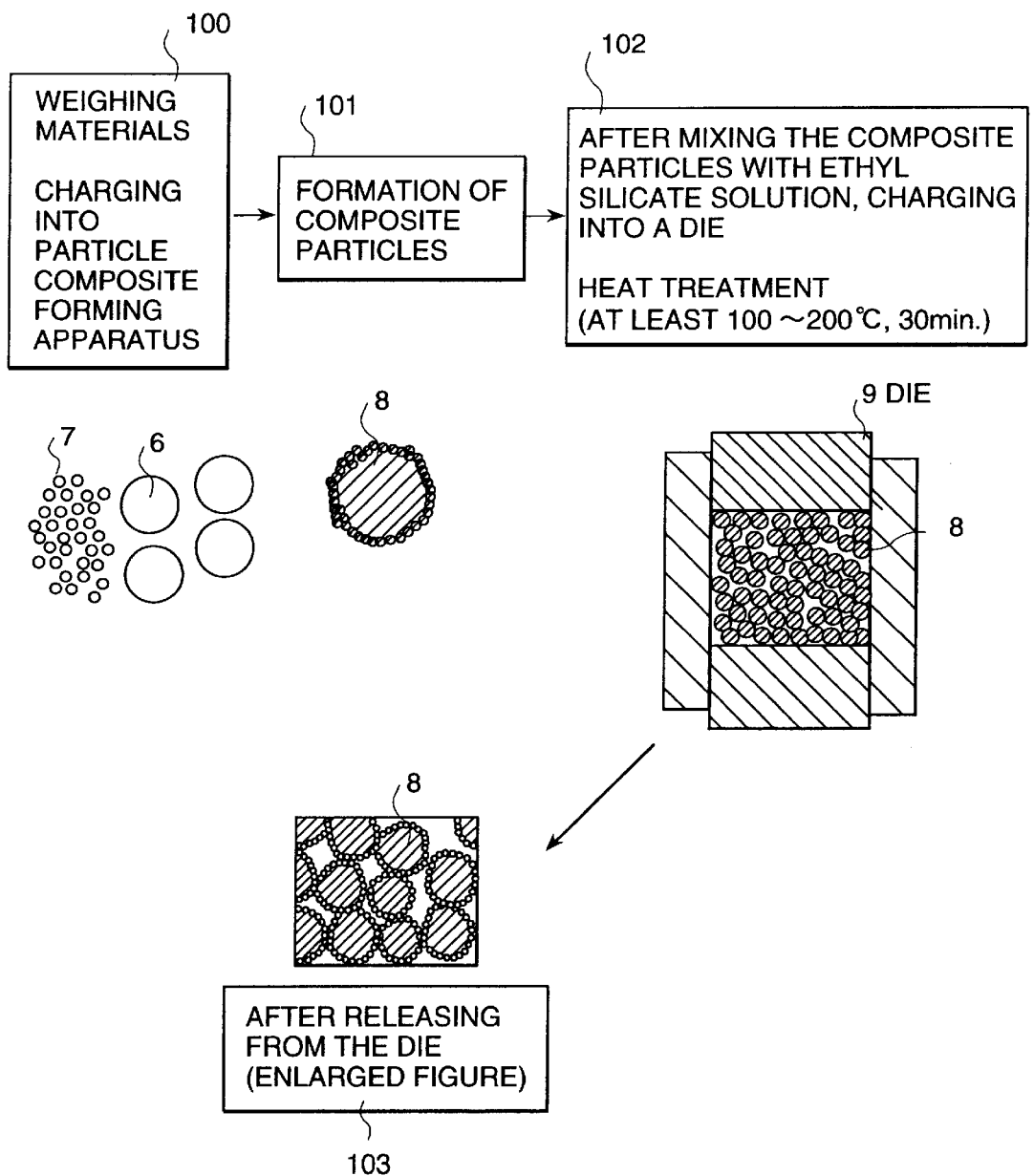
FIG. 5 is schematic illustrations for explaining the other manufacturing method of the silicon oxide composite particles structural body.

FIG. 5 is a set of schematic illustrations for explaining the other manufacturing method of the silicon oxide composite particles structural body 2. In the step 100 in FIG. 5, the resin particles 6 and silicon oxide particles 7 (average particle diameter 8–10 $\mu$m) are weighed so that the weight of the silicon oxide particles becomes 0.2–10% by weight to the weight of the resin particles 6. The weighed particles 6 and 7 are charged into a well known particle composite forming apparatus for forming a composite. In the step 101, the silicon oxide composite particles 8 are formed by the particle composite forming apparatus. The silicon oxide composite particle 8 is a composite particle, which is composed by burying plural silicon oxide particles 7 having a smaller diameter than the resin particle into the resin particle 6 having a larger diameter as indicated in FIG. 5.

In the step 102, a designated amount of ethyl silicate is added to the composite particles (silicon oxide composite particles 8). The mixture is agitated well, and charged into a die 9 made of PTFE (polytetrafluoroethylene). The charged die 9 is heated at a temperature in the range of 100° C.–200° C. for approximately 30 minutes in order to cause a condensation polymerization of the ethyl silicate in the die 9 to combine the resin particles 6 each other.

In the step 103, the structural body is taken out from the die 9. An enlarged cross section of the structural body taken out from the die 9 is shown in FIG. 5. The structural body 2 formed by the above steps is fixed to the portion corresponding to the bottom portion of the vessel 1a of the sample vessel 1, the portions other than the structural body 2 of which is previously prepared, by press fixing method or adhesion, and the like.

In accordance with the embodiment indicated in FIG. 5, the same advantages as the embodiment indicated in FIG. 4 can be obtained.

In the above embodiments, the concentration of ethyl silicate is variable. The particle size of the using silicon oxide particles 7 is desirably a value in the range from 0.001 $\mu$m to 100 $\mu$m. In the case when the diameter is smaller than 0.001 $\mu$m, the particles are scattered in the mixing operation and the concentration becomes unstable and a problem of dust is generated. Furthermore, the particles having a diameter of less than 1/10 of the diameter of the resin particle, i.e. the mother particle, are preferable as using as children particles in forming a composite. Therefore, the diameter is specified as equal to or less than 100 $\mu$m.

The resin particles 6 used in the present invention is preferably made of generally used resins such as polyethylene, polypropylene, polycarbonate, polyurethan, and fluorine group resins such as polytetrafluoroethylene (PTEF). However, the influence of the base material can be eliminated by treating its surface sufficiently with the silicon oxide, and in this case, the resin material is not restricted to the above materials.

The ethyl silicate solution (a sol-gel solution containing silicon compound) operates as a binder for combining the silicon oxide particles or composite particles each other. In the examples above, the ethyl silicate solution is used as the binder in the above embodiment. A sol gel solution of various metals can be used as the binder, but the nucleic acid capturing efficiency can be increased by using the sol gel solution containing silicon compound, because the binder portion can be used for combining the nucleic acid.

As the composition of the sol gel solution, a solution, wherein silicon alkoxide is taken as a main component, and water (for hydrolysis), acid or alkali (as catalyst), and solvent (for adjusting homogeneous solution. When alkoxide is used, alcohol is generally used) are mixed with the main component, is used. The sol gel solution is not restricted to the above composition, but carboxyl salts and inorganic compounds can be used instead of the alkoxide, and ethylene glycol, ethylene oxide, triethanolamine, xylene, and the like can be used as the solvent. Depending on necessity, an additive, for instance, an agent for preventing generation of cracks can be added.

In accordance with the present invention, filling factor of the particles in the structural body can be increased by a heat treatment of the die under a pressurized condition during the heating treatment in the step 102, and accordingly, porosity of the structural body can be adjusted to a definite value. However, in this case, the resin particle 6 itself is deformed in accordance with increasing the pressure.

Furthermore, it is possible to pressurize the structural body for a definite time before heat treatment, and the heat treatment is performed after eliminating the pressure. In this case, the filling factor is decreased to lower than a case when the heat treatment is performed under a pressurized condition, but the resin particle 6 is not deformed. The temperature of the heat treatment is varied depending on the kind of the resin particle used, and the time can be varied depending on the kind and amount of the resin particles.

When the heat treatment is performed with a die made of PTFE, temperature of which is controllable by side planes and top and bottom planes separately, the temperature at the side planes is set somewhat higher than the temperature at the top and bottom planes of the die. Accordingly, the resin particles at the side plane are fused, and unevenness of the particles can be eliminated. When the structural body is used by inserting into the sample vessel, a problem is caused by flowing the liquid sample through the gap formed between the inner wall of the sample vessel and the structural body, and disturbing an efficient contacting of the liquid sample with the structural body.

The gap formed between the inner wall of the sample vessel and the structural body can be decreased by fusing the resin particles only at the side planes to eliminate the unevenness and to make it smooth by temperature control of the die. Accordingly, the liquid sample can be contacted with the structure body more effectively, and recovery of the nucleic acid can be performed efficiently.

As one of the manufacturing methods for preparing the structural body, a method utilizing ultrasonic waves can be adopted instead of the method using the heat treatment. In this case, an ultrasonic welding is performed by inserting a horning head generating the ultrasonic waves instead of the pin of the die made of PTFE. The ultrasonic waves is transmitted to the portions, where the particles are contacted each other. The temperature of the contacted portions of the particles are elevated, and the resin is fused and combined. In accordance with this method, the treating time can be varies from several seconds to several tens seconds by setting the frequency and output adequately to respective resin.

In accordance with the present invention, the filter-shaped structural body, which can be formed in an arbitrary shape, containing silicon oxide particles having a high combination ability with the nucleic acid, and maintaining a high B/F separating velocity, and the nucleic acid separating vessel comprising the structural body can be realized, as explained above.

The present invention has solved the contradiction problem that, if the size of the silicon oxide particles is decreased in order to increase the combination ability of the silicon oxide particles with the nucleic acid, the structural body becomes a compact structure, and B/F separating velocity is decreased. Practically, the silicon oxide particles having a particle size necessary for obtaining a desired combination ability with the nucleic acid were combined with the surface of the resin particles having larger particle size than the silicon oxide particles to form the silicon oxide composite particles; the structural body was formed in an arbitrary shape using the silicon oxide composite particles by utilizing characteristics of the resin particles: and the nucleic acid separating vessel was realized by providing the structural body to the sample vessel.

In accordance with the present invention, the diameter of the silicon oxide particles, which will be the nucleus of the nucleic acid combination, and the diameter of the resin particles can be set as an arbitrary value, and various sizes of the particle diameters can be combined. Accordingly, the kind of the object of the nucleic acid separation, the kind and the amount of the nucleic acid to be recovered, and the B/F separating velocity necessary for the nucleic acid separating condition of the object can be made optimum by selecting an appropriate combination of the particle sizes.

In accordance with the present invention, simultaneous processing of multi-samples and an automatic operation can be performed readily by forming the filter-shaped structural body, which can be formed in an arbitrary shape, containing silicon oxide composite particles having a high combination ability with the nucleic acid, and providing the structural body in the nucleic acid separating vessels in a shape of micro plate, as explained above. Furthermore, shortening the operation time, saving man-hours, and an unattended operation can be realized.

The diameter of the silicon oxide particles and the diameter of the resin particles can be set with an arbitrary size as described previously, but the diameter of the silicon oxide particles are desirably smaller than $1/10$ of the diameter of the resin particles. The diameter of the silicon oxide particles are preferably in the range of 0.001 $\mu$m–500 $\mu$m, and the diameter of the resin particles are preferably in the range of 50 $\mu$m–5000 $\mu$m.

The silicon oxide group particle in the present specification is composed substantially of silicon oxide in crystalline state and other states. Generally, silica ($SiO_2$) includes various transformation. The main transformations are quartz, tridymite, and cristobalite, respective of which has a high temperature type and a low temperature type. Quarts is not a salt, but it is sometime classified as a silicate mineral based on its condensation form. Normal glass is an amorphous material stabilized by entering an alkaline metal or alkaline earth metal into three dimensional irregular net work structure of condensed silicic acid.

Furthermore, a method for forming silica by a hydrolysis reaction and a dehydro-condensation reaction using an alkoxide compound of silicon is well known. The silicon oxide described above is a nomenclature for whole material of silica, glass, silicate, silicate minerals, and crystalline and non-crystalline compounds of condensed silicic acid.

The fabrication of the silicon oxide composite particles can be achieved by a process comprising the steps of: charging the composite particles into a die; fusing and adhering the resin particles by performing a heat treatment at a temperature higher than the heat resistance temperature of the resin particles; taking out the structural body from the die; immersing the structural body into a sol gel solution containing silicon oxide; taking out the structural body from the sol gel solution; and performing a condensation polymerization reaction of the sol gel solution contained in the structural body by a heat treatment.

The fabrication of the silicon oxide composite particles can also be achieved by a process comprising the steps of: mixing the silicon oxide composite particles and the sol gel solution containing the silicon oxide; charging the mixture into a die; forming the structural body from the mixed material by a heat treatment to cause condensation polymerization of the sol gel solution; and taking out the structural body from the die.

Because the structural body has a three dimensional combination of the silicon oxide composite particles, the structural body retains a relatively high strength. Therefore, the silicon oxide composite particles seldom float in the liquid sample, an agitating operation for making the nucleic acid in the liquid sample contact uniformly with the silicon oxide composite particles is not necessary, and it is possible to make the nucleic acid in the liquid sample contact uniformly with the silicon oxide composite particles only by passing the liquid sample through the silicon oxide composite particles structural body.

It is possible to make the silicon oxide composite particle structural body have a filter-like structure, and the nucleic acid separation and the separation of floating articles in the liquid sample can be achieved concurrently.

As the nucleic acid separating vessel, which is manufactured by fabricating the silicon oxide composite particles and providing to the sample vessel, the vessels called micro plates having a same shape, which are arranged on a same supporting plate, and provided with the silicon oxide composite particles structural body therein, respectively, are preferable. As the type of fixing the structural body therein, the micro plate comprising the silicon oxide composite particles structural body therein, and an inner plate, which can be inserted into a well of the micro plate, comprising the silicon oxide composite particles structural body therein are preferable.

Furthermore, depending on the number of samples and sample volume, a composition comprising mainly micro tubes, test tubes, flasks, beakers, and others, which further comprises the silicon oxide composite particle structural body therein, can be used. The micro plates provided with the silicon oxide composite particle structural body therein are preferable for treating multi-samples simultaneously, performing an automatic operation readily, shortening the operation time, saving man-hours, and realizing an unattended operation in the separating operation of the nucleic acid.

In accordance with the present invention, the nucleic acid separating vessel, which is capable of suppressing decrease of the B/F separating velocity with maintaining the nucleic acid combining ability high can be realized, because the nucleic acid separating vessel is provided with the structural body comprising the silicon oxide composite particles, wherein a composite is formed with the plural silicon oxide particle having smaller diameter and the resin particles having larger diameter, at the bottom portion of the vessel.

The method of manufacturing the nucleic acid separating vessel, which is capable of suppressing decrease of the B/F separating velocity with maintaining the nucleic acid combining ability high, can be realized.

The method for separating nucleic acid using the nucleic acid separating vessel, which is capable of suppressing decrease of the B/F separating velocity with maintaining the nucleic acid combining ability high, can be realized.

In accordance with the present invention, the diameter of the silicon oxide particles, which will be the nucleus of the nucleic acid combination, and the diameter of the resin particles can be set as an arbitrary value, and various sizes of the particle diameters can be combined. Accordingly, the kind of the object of the nucleic acid separation, the kind and the amount of the nucleic acid to be recovered, and the B/F separating velocity necessary for the nucleic acid separating condition of the object can be made optimum by selecting an appropriate combination of the particle sizes.

Accordingly, the filter-shaped structural body, which can be formed in an arbitrary shape, containing silicon oxide particles having a high combination ability with the nucleic acid, and maintaining a high B/F separating velocity, and the nucleic acid separating vessel comprising the structural body can be provided.

Performing simultaneous processing of multi-samples and an automatic operation readily, shortening the operation time, saving man-hours, and an unattended operation of the separating operation of the nucleic acid become possible by providing silicon oxide composite particle structural body in the nucleic acid separating vessels in a shape of micro plate.

Figure 6:
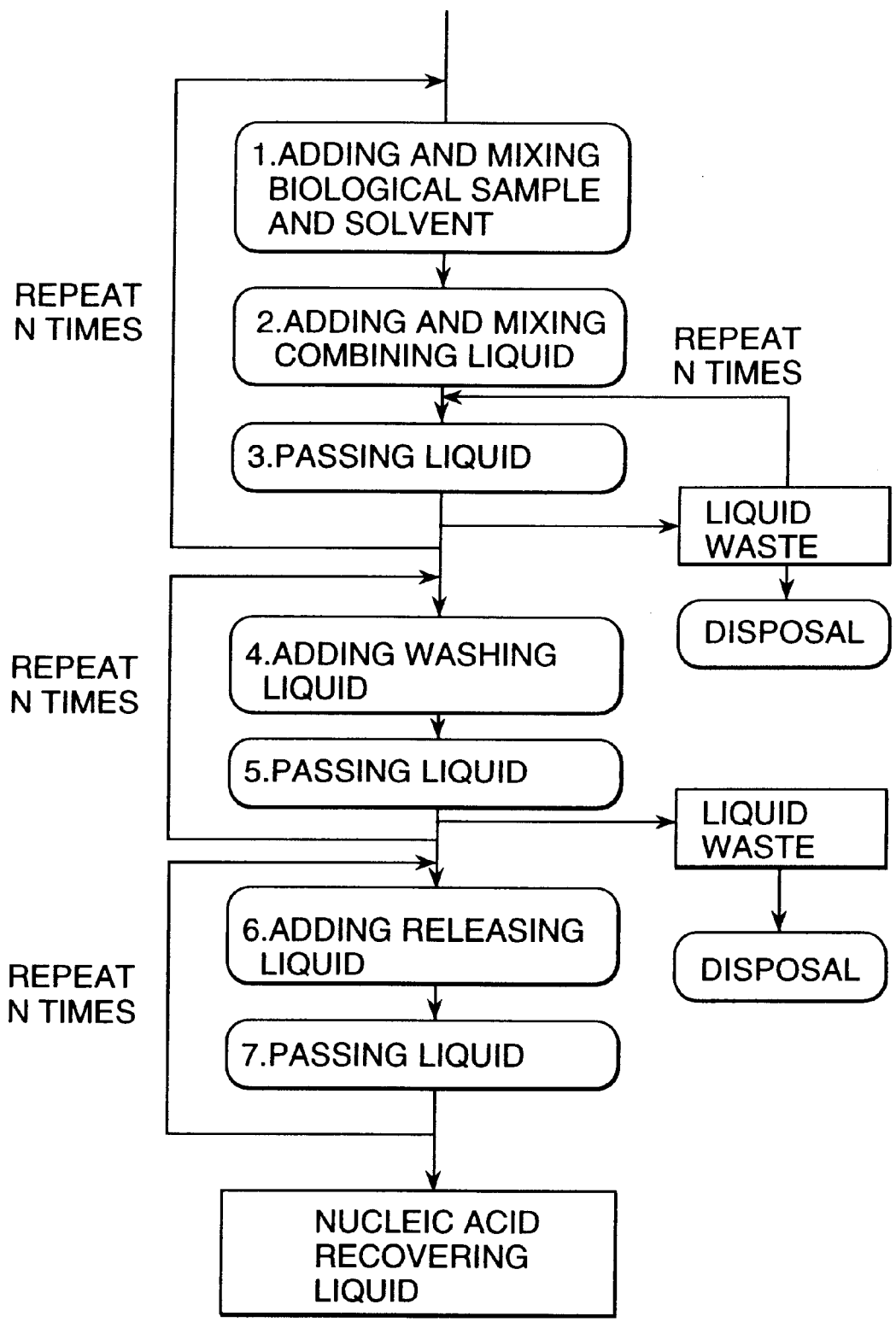
FIG. 6 is a schematic operation flow indicating an example of nucleic acid separating and purifying method using the nucleic acid separating vessel of the present invention.

FIG. 6 indicates an example of operation flow of a nucleic acid separating and purifying method using the nucleic acid separating vessel of the present invention. However, the present invention is not restricted by the figure. In the step 1 in FIG. 6, a biological sample is mixed with a dissolving liquid containing protein modifying agent, surface active agent, various enzymes, and others in a nucleic acid separating vessel, in order to make nucleic acids contained in the biological sample contact with the dissolving liquid. In the step 2, a combining liquid containing chaotropic ions and others is further added to the above mixed liquid. In the step 3, the nucleic acids contained in the above mixed liquid is combined with the silicon oxide structural body by passing the mixed liquid through the silicon oxide structural body. The step 3 can be repeated for several times, if the nucleic acids are not combined sufficiently with the silicon oxide structural body by one passing. Furthermore, the above steps from 1 to 3 can be repeated for plural times when the amount of nucleic acid combined with the silicon oxide structural body is larger than the amount of the nucleic acid in the biological sample. In the step 4, a washing liquid is added into the nucleic acid separating vessel after completing the above steps from 1 to 3. In the step 5, residual biological sample, dissolving liquid, and impurities from the combining liquid in the silicon oxide structural body are removed with liquid waste by passing the washing liquid through the silicon oxide structural body. The washing liquid can be any composition, if it does not release the nucleic acid from the silicon oxide structural body. The above steps 4 and 5 can be repeated for plural times depending on the cleaning condition of the silicon oxide structural body. In the step 6, a releasing liquid is added to the nucleic acid separating vessel. In the step 7, the nucleic acids are released from the silicon oxide structural body by passing the releasing liquid through the silicon oxide structural body, and a nucleic acid recovery liquid is obtained. The steps 6 and 7 can be repeated for plural times, if the nucleic acid recovery rate is not sufficient.

Figure 7:
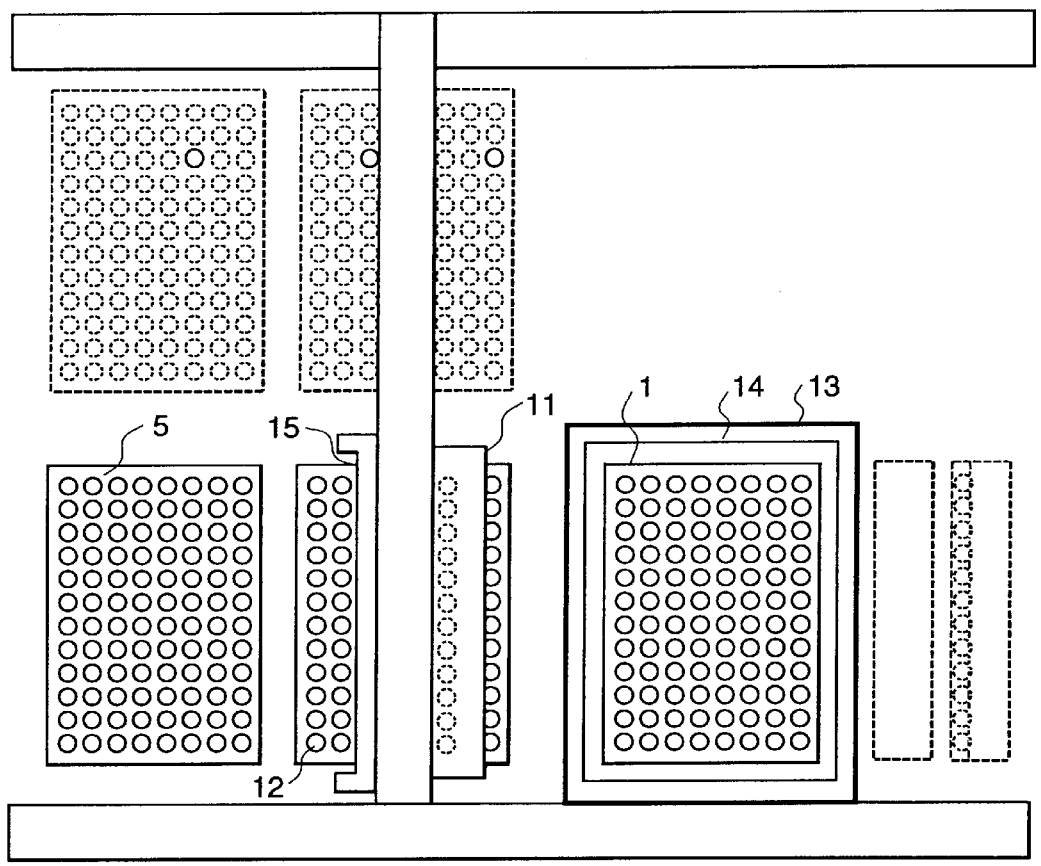
FIG. 7 is a schematic plan view indicating an example of nucleic acid separating and purifying apparatus using the nucleic acid separating vessel of the present invention.

FIG. 7 is an example of a partial plan view indicating an apparatus composition for realizing the nucleic acid separating and purifying method shown in FIG. 6. The dissolving liquid is added into the sample vessel 1 by pipetting device 11. The pipetting device 11 is desirably attachable with disposable pipetting tips, and is desirably capable of pipetting with lines for liquid transportation. A biological sample is added into the sample vessel 1 from biological sample preserving container 12, wherein the biological sample has been preserved, by the pipetting device 11, and mixed with the dissolving liquid. Similarly, a combining liquid is added to the sample vessel 1 by the pipetting device 11, and mixed with the dissolving liquid. Mixing the liquid can be achieved by sucking and discharging the liquid by the pipetting device 11, or providing a vibrator in the apparatus. The sample vessel 1 is arranged on the suction chamber 13, and the time of the step for passing the liquid can be shortened by decreasing the pressure in the suction chamber 13 using a sucking apparatus. The liquid waste is discharged from a liquid waste outlet provided in the suction chamber 13. Sometimes, the liquid waste can be recovered by providing a liquid waste recovery vessel 14 in the suction chamber 13, and the liquid waste can be passed through the sample vessel 1 repeatedly. In this case, the sample vessel 1 can be separated from the suction chamber 13 by a hand arm 15, and the liquid waste is added to the biological sample preserving container 12 from the liquid waste recovery vessel 14 by the pipetting device 11. The sample vessel 1 supported by the hand arm 15 is placed again in the suction chamber 13, the liquid waste is added as above from the biological preserving container 12 to the sample vessel 1 by the pipetting device 11.

The washing liquid is also added to the sample vessel 1 by the pipetting device 11, and passing through the sample vessel 1 as same as the above by the suction chamber 13. After completing washing, the sample vessel 1 is separated from the suction chamber 13 by the hand arm 15, and is arranged in the recovery vessel 5. The recovery vessel 5, wherein the sample vessel 1 is arranged, is arranged in the suction chamber 13 again by the hand arm 15, and the nucleic acid recovery liquid is obtained in the recovery vessel 5 by passing the liquid through the sample vessel 1 by the suction chamber 13 as same as the above. Sometimes, the releasing liquid is added into the sample vessel 1 again, the liquid is passed through the sample vessel 1 by the suction chamber 13, and the nucleic acid recovery liquid is obtained in the recovery vessel 5. The operation to place the recovery vessel 5, wherein the sample vessel 1 is arranged, in the suction chamber 13 by the hand arm 15 can be omitted by providing a suction chamber exclusive to the recovery vessel 5.

What is claimed is:

1. A nucleic acid separating apparatus comprising a supporting plate that has a plurality of vessels each forming a cavity, said cavity having a shaped composite body therein, said body comprising composite structures of silicon oxide particles supported on a resin particle having a particle size larger than that of said silicon oxide particles, wherein the composite structures are combined three-dimensionally with each other, and wherein each of said vessels has a liquid inlet atop and a liquid outlet at the bottom thereof.

2. The apparatus according to claim 1, wherein said vessels constitute an array.

3. The apparatus according to claim 1, wherein said vessels are arranged in an operational relation with a pipetting device.

* * * * *